United States Patent [19]

Rubino

[11] 4,021,536

[45] May 3, 1977

[54] MAGNESIUM-ZIRCONIUM COMPLEXES USEFUL AS ANTIPERSPIRANTS

[75] Inventor: Andrew M. Rubino, New Providence, N.J.

[73] Assignee: Armour Pharmaceutical Company, Phoenix, Ariz.

[22] Filed: Apr. 18, 1975

[21] Appl. No.: 569,248

[52] U.S. Cl. .............................. 424/47; 260/429.3; 424/66
[51] Int. Cl.² ........................................ A61K 7/34
[58] Field of Search ............ 260/429.3; 424/47, 66

[56] References Cited

UNITED STATES PATENTS

| | | | |
|---|---|---|---|
| 2,236,387 | 3/1941 | Wallace et al. | 424/68 |
| 2,814,584 | 11/1957 | Daley | 424/66 |
| 2,814,585 | 11/1957 | Daley | 424/66 |
| 2,854,382 | 9/1958 | Grad | 424/68 |
| 3,405,153 | 10/1968 | Jones et al. | 260/429.3 |
| 3,407,254 | 10/1968 | Siegal et al. | 424/66 |
| 3,792,068 | 2/1974 | Luedders et al. | 260/429.3 |

FOREIGN PATENTS OR APPLICATIONS

| | | | |
|---|---|---|---|
| 624,120 | 5/1949 | United Kingdom | 260/429.3 |

*Primary Examiner*—Helen M. S. Sneed

*Attorney, Agent, or Firm*—Frank T. Barber; William W. Schwarze

[57] ABSTRACT

Astringent compositions useful as antiperspirants are provided by forming a complex of a magnesium salt and an astringent zirconium compound, particularly zirconium oxy and hydroxy salts, such that the weight ratio of the zirconium content to the magnesium content in the complex expressed as the oxides will be in the range of about 30:1 to 1:1. The preferred amount of magnesium, expressed as the oxide, in an aqueous antiperspirant solution containing an effective amount of the complex will be greater than about 3 weight percent. Preferred compositions include complexes of magnesium-amino acid salts, such as magnesium glycinate, plus zirconyl hydroxy chloride in which the ratio of zirconium to magnesium is about 10:1 to 3:1 and the total content of magnesium plus zirconium is about 5 to 15 weight percent and preferably about 5 to 10 weight percent, both expressed as the oxides. Buffers such as urea, amino acids, salts of amino acids, etc. may also be included in the complexes to maintain a pH of at least about 3 in aqueous solutions of the complex. The various complexes of the invention may be used in conventional antiperspirant forms, including aqueous solutions, aerosol sprays, powder-in-oil aerosol sprays, creams, lotions, cream sticks, etc.

13 Claims, No Drawings

MAGNESIUM-ZIRCONIUM COMPLEXES USEFUL AS ANTIPERSPIRANTS

BACKGROUND OF THE INVENTION

The present invention relates to basic magnesium-zirconium complexes useful as antiperspirants. More particularly the invention is directed to the production of highly effective antiperspirant systems using zirconium as the primary astringent ingredient and magnesium as a buffering agent as well as a source of synergistic antiperspirant action when reacted with zirconium.

It has been known in the art for some time that zirconium salts provide exceptionally effective antiperspirant properties. Such zirconium compounds have included particularly the acidic zirconium salts, such as zirconium oxy chloride or zirconyl chloride, zirconium hydroxy chloride, and other halide and sulfate substitutes of the salts. However, the zirconium salts are extremely acidic and irritating to the skin. For example, a solution of zirconyl chloride which is effective as an antiperspirant has a pH of only about 0.8 and a solution of zirconyl hydroxy chloride which is effective as an antiperspirant has a pH of only about 1.2. As a result, it is necessary to buffer these solutions up to a pH which is suitable for application to the human skin, i.e., up to at least about 3 to 5.

A number of prior attempts have been made in the art to buffer solutions of zirconium salts or to form zirconium complexes which take advantage of the effectiveness of zirconium compounds. One early attempt included the development of sodium zirconium lactate for use in cologne-stick type formulations. This lactate complex salt was sufficiently alkaline (pH 8.5), but was ineffective as an antiperspirant, and was repeatedly implicated in the generation of "zirconium granulomas" in some users.

Other attempts to make use of the acidic zirconium salts involved the buffering of solutions of these salts with urea (see U.S. Pat. No. 2,814,584 to Daley) or water soluble amino acids (see U.S. Pat. Nos. 2,814,585 to Daley and 2,854,382 to Grad) or aluminum hydroxy halides (see U.S. Pat. No. 2,906,668 to Beekman).

More recently, various derivatives have been formed incorporating zirconium compounds, including the amine-amide derivatives of U.S. Pat. No. 3,407,254 to Siegal et al., and the polyhydroxy derivatives of U.S. Pat. No. 3,405,153 to Jones and Rubino.

In addition, Rubino copending application Ser. No. 418,712, filed Nov. 23, 1973, entitled "Aluminum-Zirconium Anti-Perspirant Systems With Salts Of Amino Acids", and other related copending applications describe other systems in which amino acids have been incorporated in aluminum-zirconium complexes to offset the acidity of the zirconium and aluminum as well as provide other advantages to the antiperspirant. Nevertheless, still more efficient and advantageous methods are being sought to combat the acidity of zirconium while at the same time maintaining or improving antiperspirant efficiency Various double salts, co-precipitates, and complexes of magnesium and aluminum have heretofore been described in the patent art and technical literature. For example, in U.S. Pat. No. 2,797,978 the preparation of hydrous gels comprising aluminum magnesium hydroxy carbonate is described including its intended use in oral administration as an antacid for treatment of peptic ulcer and other symptoms of gastric hyperacidity. Numerous other patents describe gels and gelatinous precipitates comprising magnesium and aluminum in various proportions for similar use as antacids.

It has also been proposed in U.S. Pat. No. 2,350,047, to incorporate into antiperspirant solutions or creams containing certain astringent aluminum salts, small amounts (from about 1 to 3 percent) of a water insoluble base, such as an oxide, hydroxide or carbonate of zinc, aluminum or magnesium, to reduce the deteriorating effect of these aluminum compounds upon fabrics, particularly when such fabrics are exposed to hot ironing. The incorporation of larger proportions of these basic compounds is contraindicated in the patent and is stated to reduce the perspiration inhibiting effect of the astringent salt.

In accordance with U.S. Pat. No. 2,571,030, the corrosive effects on fabrics of antiperspirant cream compositions containing aluminum chlorohydroxide or aluminum chloride, can be reduced by forming a water-dispersible double complex of the aluminum chloride with calcium chloride or with chlorides of other bivalent or monovalent metals. Examples of such other metal chlorides suggested in the patent, are those of the alkali metals, of zinc and of magnesium. Such added metal halides are advocated to be employed in the proportion of 0.2 to 15 parts by weight to 100 parts of aluminum, each being calculated as the element (corresponding to a maximum of less than 7 parts CaO or MgO per 100 parts of $Al_2O_3$).

BRIEF SUMMARY OF THE INVENTION

In accordance with the present invention, astringent complexes are prepared by dissolving in aqueous or alcoholic solution controlled proportions of a magnesium compound and an acidic (cationic) or astringent zirconium compound. Solutions containing such complexes of zirconium and magnesium compounds in the weight ratio, determined as their oxides ($ZrO_2$ and MgO), in the range of about 30:1 to 1:1, exhibit excellent antiperspirant activity. That is, at a total concentration in water of 5 to 10 weight percent of total magnesium and zirconium (both expressed as oxides) these compositions are comparable or superior in antiperspirant activity to standard aluminum chlorhydrate solutions. The obtained solutions may be incorporated as such into antiperspirant formulations or dried to form powders for incorporation into various conventional antiperspirant formulations, as will hereinafter appear. The 5 to 15 weight percent, calculated as oxides, aqueous solutions have a pH above 3, preferably about 3 to 5, and the corresponding alcoholic solutions have an apparent pH above 2.

Aside from the $ZrO_2$/MgO ratio of the complexes, the preferred makeup of the complex should be such that an aqueous antiperspirant solution containing an effective amount of the complex will contain greater than about 1 weight percent, and preferably greater than about 3 weight percent, magnesium, expressed as the oxide, based on the weight of the solution, as distinguished from the solutions of U.S. Pat. No. 2,350,047 to Klarmann et al. which do not contain zirconium and contain about 1 to 3 weight percent of an insoluble magnesium compound to reduce the deteriorating effects of aluminum chloride or sulfate antiperspirants.

DETAILED DESCRIPTION OF PREFERRED EMBODIMENTS

The acidic or cationic zirconium compounds which may be used in the complexes of the present invention include both the zirconium oxy salts and zirconium hydroxy salts, also referred to as the zirconyl salts and zirconyl hydroxy salts. These compounds may be represented by the following general empirical formula:

$$ZrO(OH)_{2-nz} B_z$$

wherein z may vary from about 0.9 to 2 and need not be an integer, n is the valence of B, 2-nz is greater than or equal to 0, and B is selected from the group consisting of halide, nitrate, sulfamate, sulfate and mixtures thereof. It will be understood that other Group IV B metals, including hafnium could also be used.

It will be understood that the above formula is greatly simplified and is intended to represent and include compounds having coordinated and/or bound water in various quantities, as well as polymers, mixtures and complexes of the above. For example, the oxy group in the above general formula could instead be indicated with a water molecule bound to the compound and written as two OH groups. Thus, zirconyl hydroxy chloride could be written as $Zr(OH)_3Cl$ instead of $ZrO(OH)Cl$. similarly, zirconyl chloride may be written as either $ZrOCl_2$ or $Zr(OH)_2Cl_2$. As will be seen from the above general formula, in which the oxy group is represented as O rather than $(OH)_2$, the zirconium hydroxy salts actually represent a range of compounds having various amounts of the hydroxyl group, varying from about 1.1 to only slightly greater than 0 groups per molecule.

Particularly preferred zirconium compounds for use in the complexes of the present invention include zirconyl chloride (also referred to as basic zirconium chloride or zirconium oxy chloride) and zirconyl hydroxy chloride, which may be represented by the simple formulas $ZrOCl_2$ and $ZrO(OH)Cl$, respectively. These compounds are commercially available in solution form. In the alternative, the zirconium compounds can be made by dissolution of commercially available zirconium carbonate paste (carbonated hydrous zirconia) in the appropriate amount of the acid of the anion to be used, e.g. hydrochloric acid. Other useful zirconium salts will be apparent to those of ordinary skill in the art, such as trioxodizirconium hydroxy halides and similar salts described in U.S. Pat. No. 2,837,400 to Blumenthal, for example.

Additional sources of zirconium for use in forming the complexes of the present invention may include alkali metal and ammonium zirconyl carbonate (AZC) and basic zirconium gels. However, these compounds are generally not suitable for use alone as the source of zirconium, but should be used in combination with at least one of the abovementioned zirconium salts, such as zirconium hydroxy chloride.

Ammonium zirconyl carbonates and alkali metal zirconyl carbonates, such as potassium zirconyl carbonate, and complexes thereof useful as antiperspirants, are described in my copending application Ser. No. 552,823, filed Feb. 25, 1975, entitled "Alkali Metals And Ammonium Zirconyl Carbonate Complexes Useful As Antiperspirants". AZC may be prepared according to several methods, such as described in German patent publication No. 2,251,434, published May 3, 1973 or U.S. Pat. No. 3,418,073 to Blumenthal.

Basic zirconium gels, such as basic zirconium carbonates, zirconium hydroxide and basic zirconium-amino acid compounds, including particularly basic zirconium glycinate, and complexes thereof useful as antiperspirants are disclosed in copending patent application Ser. No. 562,300 of Rubino et al., filed Mar. 26, 1975, entitled "Basic Zirconium Complexes And Methods Of Making And Using In Antiperspirants". Basic zirconium carbonate gels may be prepared by standard precipitation techniques using sodium carbonate and most any of the usual zirconium oxy or zirconium hydroxy salts previously referred to, such as zirconyl chloride or zirconyl hydroxy chloride. Basic zirconium-amino acid gels may be formed by the usual method of reacting zirconyl chloride or zirconyl hydroxy chloride with the desired amino acid. However, according to application Ser. No. 562,300, such gels are preferably prepared by reacting in aqueous medium a water soluble salt of an amino acid and a water soluble zirconium salt, which results in the precipitation of a basic zirconium-amino acid gel.

The magnesium compounds that may be employed may be soluble or insoluble and include the halides, nitrates, sulfamates, sulfates, phenolsulfonates, carbonates, hydroxides, oxides and admixtures of these. It will be understood that the water insoluble magnesium compounds, such as magnesium oxide, hydroxide and carbonate, become solubilized when reacting with the acidity generated by hydrolysis of the zirconium compounds to form soluble complexes.

Preferred magnesium compounds for use in preparing the complexes of the present invention are the magnesium salts of amino acids, particularly salts of the so-called neutral amino acids which contain amino groups for each carboxyl group in the acid molecule. Such amino acids include glycine, β-alaninate, L-proline, β-arginine, etc. Particularly prefered salts of amino acid include magnesium glycinate and magnesium β-alaninate. The salts of the amino acids may be alkaline or hydroxy salts of amino acids, such as described in my copending application Ser. No. 418,712 referred to above.

Other suitable magnesium compounds for use in preparing the complexes of the present invention include magnesium salts of hydroxy carboxylic acids. Suitable hydroxy carboxylic acid salts include salts of hydroxy acids having a hydroxyl group alpha and/or beta to the carboxylic acid radical. Examples of such acids include lactic, citric, tartaric, glycolic, gluconic, trihydroxyglutaric, citryl trigulconic, citryl mono gluconic, citryl digluconic, malic, tetrahydroxy adipic, and citramalic acids, and mixtures thereof. These salts may be obtained commercially or prepared by reacting the desired hydroxy carboxylic acid with magnesium hydroxide, oxide, carbonate or bicarbonate. These salts and complexes thereof useful as antiperspirants are disclosed in my copending application Ser. No. 433,931, filed Jan. 16, 1974 for "Aluminum-Zirconium Antiperspirant Systems With Hydroxy Carboxylic Compounds".

With the complexes formed according to the present invention it may be necessary to also include a stabilizing agent or buffer to yield a stable solution and desirable solution pH of at least about 3. Many suitable buffers are known in the art (see for example the Grad and Daley patents referred to above), and other (described in copending applications) have been recently developed. Suitable buffers, which may simply be added to the reaction solution, include urea, amino acids, alkaline and hydroxy salts of amino acids (see copending application Ser. No. 418,172 of Rubino), hydroxy carboxylic acids and salts thereof, etc. It is preferable that any added buffer be kept to a minimum and preferably less than about 15 weight percent of the complex.

In general, the relative amounts of the zirconium compound and magnesium compound to be reacted together should be as to yield a $ZrO_2/MgO$ ratio of between about 30:1 to 1:1, and preferably 10:1 to 3:1. Although relatively high ratios of zirconium are desirable from the standpoint of antiperspirant efficacy, such ratios are sometimes contraindicated due to the greater cost of zirconium. In addition, large amounts of zirconium usually increase the possibilities of skin irritation, though these may be mitigated by the buffering action of the hydroxyl and amino acid groups, such as those in the above buffers. Further, the MgO content of an aqueous solution of the complex should be at least about 1 and preferably greater than 3 weight percent.

The method of forming the complexes of the present invention is not particularly critical. The various components are preferably added one at a time, and stirring and/or moderate heating or even refluxing may be advantageous or even necessary to complete reaction of certain ingredients, particularly during and after addition of insoluble zirconium compounds.

The drying of the finished prepared antiperspirant complexes of the invention is not particularly critical and may be carried out in a number of different ways, including vacuum drying, oven drying, spray drying or freeze drying. It will be understood that drying does not mean that all of the water is removed, since a certain amount of water should remain in the complex as coordinated and/or bound water. Thus, drying to just past the point where the solution becomes a friable solid should be sufficient. If the complex is over dried, so that some of the coordinated and/or bound water is removed, the stability and/or activity of the complex may be interfered with, and the complex may not be readily redissolvable in solvents, particularly hydroalcoholic solvents.

While it has been indicated that the reaction process is not considered particularly critical, it will be understood that sufficient time, heat and agitation are needed to allow reaction of the compounds to form the new complexes of the present invention. This is particularly so in the case of insoluble zirconium compounds used to form complexes of this invention.

Also, it will be understood that not all possible combinations of the magnesium compounds and astringent zirconium compounds in the classes listed above are suitable for reaction in forming complexes of the present invention. For example, most combinations of zirconyl hydroxy chloride and magnesium chloride, alone or with salts of hydroxy carboxylic acids as buffers, yield complex solutions which are too acidic. Zirconium hydroxy chloride and magnesium sulfamate do not form stable complexes, and magnesium hydroxide cannot be sufficiently dissolved in a solution of zirconyl hydroxy chloride. Also, complexes can be formed between magnesium carbonate and zirconyl chloride, zirconyl nitrate, etc., but the solutions tend to gel and the complexes cannot be fully reconstituted in water. The above examples and similar combinations are more the exception than the rule, and even where it is not possible to fully reconstitute the complexes in water, the original reaction solutions may often be used as is.

Preparations of the initial solutions and dried powders useful in practice of the invention are described in the examples below by way of illustration without being limited thereto.

EXAMPLE I

Twenty grams of TDHCl solution (trioxodizirconyl hydroxy chloride; 5.2% Zr) was diluted with 150 g. of water. The pH of this solution was equal to 2.5. To the above solution was added 50 g. of a 10% magnesium glycinate slurry (obtained from J. H. Walker and Company; 1.3% Mg). The solution was warmed at 50° C. for 30 minutes. The resultant clear solution has a pH of 4. The product was then oven-dried at 50° C. under a vacuum of 35 cm. of Hg. The dried material contained 3.42% Mg, 54.7% Zr and 18.9% glycine.

EXAMPLE II

Ten grams of $MgCl_2 \cdot 6H_2O$ was dissolved in 100 g. of a zirconyl hydroxychloride solution [Zro(OH)Cl; 7.2% Zr]. The pH of this solution was less than 1. On dissolution of 9 grams of $\beta$-alanine, the pH rose to 3.5. The product was oven-dried at 50° C. under a vacuum of 46 cm. of Hg. The dried material contained 24.1% Zr, 4.1% Mg. and 31.1% $\beta$-alanine.

EXAMPLE III

Five grams of glycine was dissolved in 100 grams of water, and 3 grams of $MgCO_3$ N.F. was added. The resulting slurry was agitated at 80° C. for ½ hour. After cooling to room temperature, 100 grams of 33-⅓ weight percent aqueous solution of zirconyl hydroxy chloride was added to the slurry with agitation. The resulting clear solution had a pH of 3.4. The solution was vacuum dried to a friable solid, and 25 grams of the solid was dissolved in 225 g of water to form a 10% w/w solution with a pH of 3.85. The solution analyzed: 0.38% Mg, 1.2% glycine and 3.6% Zr.

EXAMPLE IV

Forty grams of a 10% w/w solution of $MgSO_4 \cdot 7H_2O$ was added to a 100 g. of a 33-⅓% solution of ZHC [ZrO(OH)Cl, 14.2% Zr]. Twenty grams of glycine was then dissolved in the above solution. The pH increased to 3.3. The product was oven-dried at 45° C. under a vacuum of 41 cm. of Hg and found to contain 0.7% Mg, 25.5% Zr, and 36.2% glycine.

EXAMPLE V

Sodium $\beta$-alaninate was prepared by reacting 3 g. of $\beta$-alanine with 2.79 g. of 50% NaOH in 20 grams of water. The above was added very slowly and with vigorous agitation to 100 g. of a zirconyl hydroxychloride solution (8.5% Zr). Fifty grams of a 10% w/w solution of $MgCl_2 \cdot 6H_2O$ was then added to the above. The pH of the resultant solution was 3.2. The solution was evaporated at 55° C. under a vacuum of 45 cm. of Hg. The product analyzed: 23.0% Zr, 2.3% Mg, and 11.9% $\beta$-alanine.

EXAMPLE VI

Magnesium glycinate was prepared by reacting 1.8 g. of basic magnesium carbonate (26.1% Mg) with 3 g. of glycine in 30 g. of water, while agitating at 75° C. for one half hour. To the cooled slurry was added 50 g. of zirconyl nitrate solution [$ZrO(NO_3)_2$; 4.27% Zr] with agitation. The resultant clear solution had a pH of 3.2. The product was oven-dried at 55° C. under a vacuum of 35 cm. of Hg and found to contain 22.8% Zr, 4.79% Mg and 30.6% glycine.

EXAMPLE VII

To 102 g. of a 2% w/w slurry of $Mg(OH)_2$ was added 110 g. of zirconyl hydroxybromide solution [ZrO(OH)Br; 14.1% Zr] with agitation. Five grams of glycine was dissolved in the above solution. The product was oven-dried at 55° C. under a vacuum of 38 cm. of Hg and found to contain 2.0% Mg, 35.0% Zr and 10.8% glycine. On reconsitution to 20% w/w, the solution had a pH of 4.0.

EXAMPLE VIII

Five grams of $MgCl_2.6H_2O$ was dissolved in 100 g. of zirconyl hydroxychloride solution (7.1% Zr). The pH of this solution was 0.4. With agitation, 30 g. of calcium gluconate was then added to the above. The resultant solution was cloudy and only had a pH of 1.8. On heating to 70° C., the solution cleared and 6 more grams of calcium gluconate were added. The solution was cooled and then filtered to remove insoluble materials. The pH of the filtrate was 3.1. The solution was oven-dried at 52° C. under a vacuum of 50.5 cm. of Hg. The product analyzed: 11.0% Zr, 1.1% Mg and 6.15% Ca.

EXAMPLE IX

Magnesium glycinate was prepared by reacting 3 g. of basic magnesium carbonate (26.1% Mg) with 5 g. of glycine in 40 g. of $H_2O$, while agitating at 75° C. for one half hour. To the cooled slurry was added 100 g. of 33-⅓% zirconyl hydroxychloride solution (4.4% Zr) with agitation. After 15 minutes of stirring, the solution cleared and had a pH of 3.4. The product was oven-dried at 50° C. under a vacuum of 35 cm. of Hg, and found to contain 2.06% Mg, 36.9% Zr, and 13.1% glycine.

EXAMPLE X

To 40 g. of a 10% w/w slurry of magnesium citrate was added 100 g. of zirconyl chloride solution (5.74% Zr) with agitation. After 5 minutes of stirring, the solution cleared. The resultant solution was heated to 80° C. and then reacted with 40 g. of a basic zirconium glycinate gel (9.2% Zr, 0.62% glycine). Twenty-five grams of glycine was then dissolved in the cooled solution. The solution's pH was 3.2. The product was evaporated in an oven at 50° C. under a vacuum of 35 cm. of Hg. The material analyzed: 14.7% Zr, 0.5% Mg, and 39.6% glycine.

EXAMPLE XI

Magnesium β-alaninate was prepared by reacting 3.6 g. of β-alanine with 1.8 g. of basic magnesium carbonate in 40 g. of water, while agitating at 75° C. for one half hour. To the cooled slurry was added 2.5 g. of sodium tartrate. After five minutes of stirring, 80 g. of zirconyl hydroxychloride solution (14.4% Zr) was added to the above slurry with agitation. The solution cleared on stirring and had a final pH of 3.3. The product was oven-dried at 55° C. under a vacuum of 40 cm. of Hg and found to contain 33.1% Zr, 1.3% Mg, 1.4% Na, and 10.3% β-alanine.

EXAMPLE XII

A potassium lactate solution was prepared by reacting 50 g. of 44% lactic acid with 15 g. of 85% KOH pellets. To this solution was added 180 g. of zirconyl bromide solution ($ZrOBr_2$, 4.32% Zr) with agitation. Thirty-six grams of a 33-⅓% w/w solution of $MgSo_4.7H_2O$ was added to the above clear solution. The resultant pH was 4.2. The solution was evaporated in an oven at 55° C. under a vacuum of 35 cm. of Hg. The product analyzed: 14.3% K, 13.4% Zr, and 1.17% Mg.

As indicated previously, the complexes of the present invention may be used in a variety of conventional antiperspirant forms which are applied to the human axilla for effective perspiration inhibition. In such formulations, the complex should be present in amounts of about 1.5 to 15 weight percent (depending on the type of formulation employed).

For example, aqueous solutions of the complexes may be used in lotions, oil/water creams, and co-dispensing aerosols. The complexes of the present invention are not as a rule soluble in pure alcoholic solvent systems. However, the complexes may be considered for use in hydro-alcoholic mixed solvents, such as 50 percent ethanol and 50 percent water. In either the aqueous solutions or the hydro-alcoholic solvents, the complexes of the present invention should be present in the above antiperspirant forms in amounts of about 5 to 15 weight percent of the active ingredient (calculated on a solids basis).

Solutions which are preferred and which conform to the desired pH range include those containing 5 to 15 percent total by weight of zirconium and magnesium compounds (expressed as their oxides, $ZrO_2$ and MgO), and greater than 3 weight percent magnesium, calculated as the oxide. A preferred composition is one comprising an aqueous solution of magnesium glycinate plus zirconium hydroxy chloride wherein the ratio of zirconium to magnesium is in the range of about 10:1 to 3:1 and the total content of magnesium and zirconium is from about 5 to 10 percent both expressed by weight of their oxides. Despite the fact that magnesium compounds in themselves display little or no effective antiperspirant activity, the preferred compositions containing no more than 10 percent of the zirconium and magnesium compounds (as their oxides), have been found to be as effective or superior to standard basic aluminum chloride (aluminum chlorhydrate) solutions.

The complexes of the present invention may also be used in the now popular powder-in-oil aerosol sprays. The powder-in-oil systems comprise the dispersion of a finely divided anti-perspirant powder, such as the dried complexes of the present invention, in a non-solubilizing polar organic liquid such as an ester which serves as both a dispersion medium as well as an emollient. The organic liquid coats or wets the powder particles to render them heavier and more occlusive and/or substantive to the axillary region. This primary powder-in-oil suspension, known as the "concentrate", may also include a suspending or anti-compaction agent such as Cab-O-Sil or Bentone 34, to inhibit the dispersed phase from settling the compacting irreversibly. The so-called "extra-dry" formulations use less emollient and higher levels of dry powder, such as talc. Finally, after dynamic agitation the viscous concentrate is generally mixed with about 9 times its weight of a blend of standard propellants.

When used in the powder-in-oil aerosol sprays, the complexes of the present invention should be present in the finished formulation to the extent of about 1 to 6 weight percent, and preferably about 1.5 to 3 weight percent, total aluminum plus zirconium, calculated as the oxides. A typical powder-in-oil aerosol suspension would employ about 5 percent w/w of the active ingredient (dried complex) or about 2.5 percent total oxides.

Typical antiperspirant formulations employing the complexes of the present invention are exemplified in Table I.

TABLE I

ANTIPERSPIRANT FORMULATIONS

| Ingredient | A* Powder -in-oil aerosol | B* Powder -in-oil extra-dry aerosol | C Spray: (Manual-Pump) | D Oil-in-water lotion | E Oil-in-water cream |
|---|---|---|---|---|---|
| Active Ingredient (Antiperspirant) | | | | | |
| Complex of Ex. I | 3.5 | | | | |
| Complex of Ex. VII | | | 10.0 | | |
| Complex of Ex. II | | 5.0 | | | |
| Complex of Ex. IX | | | | 18.0 | 15.0 |
| Isopropyl Myristate | 6.0 | 3.0 | | | |
| Cab-O-Sil M-5 (1) | 0.3 | 0.5 | | | |
| Perfume | 0.2 | | 0.5 | q.s. | q.s. |
| Propylene Glycol | | | 15.0 | | |
| Propellant 11 (trichlorofluoromethane) | 45.0 | 45.0 | | | |
| Propellant 12 (dichlorodifluoromethane) | 45.0 | 45.0 | | | |
| Water | | | 49.5 | 66.0 | 56.0 |
| Alcohol SD-39C | | | 25.0 | | |
| Talc, U.S.P. | | 1.5 | | | |
| Arlacel 165 (4) | | | | | 18.0 |
| Amerchol L-101 (2) | | | | 5.0 | |
| Solulan 98 (2) | | | | 2.0 | |
| Myrj 52 (4) | | | | 4.0 | |
| Cetyl Alcohol | | | | 2.0 | |
| Glycerin | | | | 2.0 | 5.0 |
| Veegum HV (3) | | | | 1.0 | |
| Preservative | | | | q.s. | q.s. |
| Spermaceti | | | | | 5.0 |
| Titanium Dioxide | | | | | 1.0 |

(1) Cab-O-Sil M-5 - fumed amorphous silica of Cabot Corp.
(2) Amerchol L-101 and Solulan 98 - lanolin derivatives of Amerchol, Inc.
(3) Veegum HV - product of R. T. Vanderbilt & Co.
(4) Arlacel 165 and Myrj 52 - non-ionic emulsifiers of ICI America, Atlas Chem., Div.
*For "powder-in-oil" aerosols, active ingredient powders are ground before use in a micronizer to yield powders containing a particle size greater than 97% through a 325 mesh screen (44μ).

In order to test the antiperspirant efficacy of the complexes of the present invention, several aqueous antiperspirant solutions, including one made according to the present invention, were tested by an independent testing laboratory. The testing procedure was similar to that described in detail in copending application Ser. No. 411,995 of Rubino for "Basic Magnesium-Aluminum Compositions Useful As Antiperspirants".

A complex solution according to the present invention was tested against a basic aluminum chloride solution as a standard or reference. The test samples included the following:

Sample R — A 10 weight percent aqueous solution of Chlorhydrol(5/6 basic aluminum chloride) was used as the standard or reference solution.

Sample E — A Complex according to my copending application Ser. No. 562,300, filed Mar. 26, 1975, entitled "Basic Zirconium Complexes and Methods on Making and Using in Antiperspirants" was prepared by reacting 52 grams of a basic zirconium glycinate gel (9.1% Zr, 2.5% glycine) with 40 grams of $AlCl_3$ solution (2% Al). The mixture was refluxed at 80° C. until the solution cleared. The resulting solution has a pH of 3.1. The material was dried in an oven at 50° C. under a vacuum of 45 cm of Hg. The product assayed 4.2% Al, 28.2% Zr and 11.0% glycine (Al/Zr ratio = 0.5:1). A 10% w/w aqueous solution was prepared for testing by dissolving 20 grams of the product in 180 grams of water. The clear solution has a pH of 3.5.

Sample H — A sample according to the present invention was prepared from zirconium hydroxy chloride and magnesium glycinate according to Example III.

The above sample according to the present invention was tested against the standard or reference solution using a group of 13 women from the Miamiville, Ohio area. The study was carried out in five one week periods, with a two-week rest period between the test weeks. During the first week, the group was tested with the reference solution, and during each of the remaining four test weeks, the group was tested with one of four other antiperspirant solutions, which included among them the above sample according to the present invention.

The test solutions were applied by means of cotton swabs in 0.5 ml portions. During the first test week, four separate applications of the reference solution were made, and in each of subsequent test weeks five separate applications of one of the other four solutions were made. Sweat collections were made before the first application as a control, 22 hours after the last application, and 1 hour after each of the other applications.

The average percentages of sweat reduction, together with the calculated 95% confidence limits, are given below.

| | % Sweat Inhibition | | | | |
|---|---|---|---|---|---|
| Sample | 1 hr. after appl'n No. 2 | 1 hr. after appl'n No. 3 | 1 hr. after appl'n No. 4 | Means of 1 hr. collections | 22 hrs. after last appl'n |
| R | 26.3 ± 9.8 | 33.8 ± 10.4 | — | 30.0 ± 8.6 | 27.8 ± 10.0 |
| E | 42.7 ± 7.8 | 50.2 ± 8.6 | 45.1 ± 8.8 | 45.7 ± 8.0 | 45.2 ± 9.0 |
| H | 40.9 ± 9.0 | 42.2 ± 10.6 | 43.9 ± 8.0 | 42.3 ± 8.6 | 39.0 ± 8.6 |

A demonstrated sweat inhibition of more than about 20 percent on a repeated application is regarded as substantially effective. The measurement usually considered quite important is the one taken 22 hours after the last application. It is significant that the complex solution of the present invention tested above showed improved antiperspirant efficacy over the 10 percent basic aluminum chloride solutions used as the reference. There was no evidence of axillary irritation during any of the tests.

One of the advantages obtained by the addition of the magnesium compound to the compositions containing the astringent zirconium compound is reduced cost of the composition at the same antiperspirant activity. By replacement of part of the needed amount of zirconium compound by the magnesium compound considerable savings in cost are obtained since the initial cost of the zirconium compound is many times that of the magnesium compound at the same oxide content.

The present invention may be embodied in other specific forms without departing from the spirit of essential attributes thereof, and, accordingly, reference should be made to the appended claims, rather than to the foregoing specification as indicating the scope of the invention.

I claim:

1. An astringent, water-soluble complex formed by reacting in an aqueous solution:
    a. a zirconium compound selected from trioxodizirconium hydroxy salts and the group having the general empirical formula:

$$ZrO(OH)_{2-nz}B_z$$

wherein z may vary from about 0.9 to 2 and need not be an integer, n is the valence of B, 2-nz is greater than or equal to 0, and B is selected from the group consisting of halide, nitrate, sulfamate, sulfate and mixtures thereof; and
    b. a magnesium compound comprising a magnesium-amino acid salt; said zirconium and magnesium compounds being present in amounts such that the weight ratio of zirconium to magnesium expressed in terms of the oxides as $ZrO_2/MgO$ is in the range of about 30:1 to 1:1.

2. An antiperspirant composition wherein the complex of claim 1 is dissolved in a non-toxic dermatologically acceptable solvent for said complex, the magnesium compound and the zirconium compound are present in amounts such that the total magnesium plus zirconium content expressed as the oxides is about 5 to 15 weight percent, and the magnesium content is greater than about 3 weight percent expressed as the oxide.

3. An astringent complex according to claim 1 wherein the zirconium compound comprises zirconium hydroxy chloride.

4. An astringent complex according to claim 1 wherein the magnesium compound comprises magnesium glycinate.

5. An astringent complex according to claim 1 wherein the magnesium compound is magnesium glycinate and the zirconium compound is zirconium hydroxy chloride.

6. An astringent complex according to claim 5 wherein the $ZrO_2/MgO$ weight ratio is in the range of about 10:1 to 3:1.

7. An astringent complex according to claim 5 wherein the total content of magnesium plus zirconium expressed as the oxides is about 5 to 10 weight percent.

8. An astringent complex according to claim 1 wherein the complex also includes a buffer to maintain the pH of a 5 to 15 weight percent aqueous solution of the complex at at least about 3.

9. A method of inhibiting perspiration comprising applying a perspiration inhibiting amount of the composition of claim 2 to the human axilla.

10. A method of inhibiting perspiration comprising applying a perspiration inhibiting amount of a solution or suspension of the complex of claim 5 to the human axilla.

11. A method of inhibiting perspiration comprising suspending the dired complex of claim 1 in an aerosol propellant, said complex being present in the aerosol propellant to an extent of about 1 to 6 weight percent of the propellant, and spraying the resulting suspension on the human axilla.

12. An astringent complex according to claim 1 wherein said zirconium compound also includes a source of zirconium selected from the group consisting of ammonium zirconyl carbonate, alkali metal zirconyl carbonate and basic zirconium gels.

13. An astringent complex according to claim 1 wherein said magnesium-amino acid salts comprise magnesium or magnesium-hydroxy salts of amino acids having an amino group for each carboxyl group in the acid molecule.

* * * * *